United States Patent
Nakanishi et al.

(10) Patent No.: US 10,383,609 B2
(45) Date of Patent: Aug. 20, 2019

(54) SURGICAL INSTRUMENT FOR MAKING INCISIONS

(71) Applicants: PUBLIC UNIVERSITY CORPORATION NARA MEDICAL UNIVERSITY, Nara (JP); NARA SEIKO INC., Nara (JP)

(72) Inventors: Yasuaki Nakanishi, Nara (JP); Akinobu Hakoda, Nara (JP); Keiko Matsuyoshi, Nara (JP)

(73) Assignees: PUBLIC UNIVERSITY CORPORATION NARA MEDICAL UNIVERSITY, Nara (JP); NARA SEIKO INC., Nara (JP)

( * ) Notice: Subject to any disclaimer, the term of this patent is extended or adjusted under 35 U.S.C. 154(b) by 193 days.

(21) Appl. No.: 15/312,164

(22) PCT Filed: Dec. 24, 2014

(86) PCT No.: PCT/JP2014/084150
§ 371 (c)(1),
(2) Date: Nov. 17, 2016

(87) PCT Pub. No.: WO2016/103366
PCT Pub. Date: Jun. 30, 2016

(65) Prior Publication Data
US 2017/0086803 A1  Mar. 30, 2017

(51) Int. Cl.
*A61B 17/00* (2006.01)
*A61B 17/3209* (2006.01)
(Continued)

(52) U.S. Cl.
CPC ........ *A61B 17/00008* (2013.01); *A61B 17/32* (2013.01); *A61B 17/3209* (2013.01);
(Continued)

(58) Field of Classification Search
CPC .......... A61B 17/00008; A61B 17/3209; A61B 17/3211; A61B 17/32; A61B 2017/3407;
(Continued)

(56) References Cited

U.S. PATENT DOCUMENTS 2,402,306 A * 6/1946 Turkel ............... A61M 5/32
128/DIG. 26
2,525,398 A * 10/1950 Collins ............... A61M 5/00
128/DIG. 26
(Continued)

FOREIGN PATENT DOCUMENTS

JP  3736877  1/2006
JP  2012-502688  2/2012
(Continued)

OTHER PUBLICATIONS

International Search Report and Written Opinion for PCT App No. PCT/JP2014/084150 dated Apr. 7, 2015, 9 pgs.
(Continued)

*Primary Examiner* — Julian W Woo
(74) *Attorney, Agent, or Firm* — Procopio, Cory, Hargreaves & Savitch LLP

(57) ABSTRACT

To provide a surgical instrument for performing incision that enables surgery to be performed safely and easily, with minimal invasiveness and a reduced risk of damaging a tissue, such as a tendon, nerve, or blood vessel. This surgical instrument enables a tendon sheath and an aponeurotic membrane to be incised safely without significantly incising the skin or subcutaneous tissue, and makes it possible to conduct surgery percutaneously at an extremely low level of invasion.

9 Claims, 4 Drawing Sheets

(51) Int. Cl.
*A61B 17/3211* (2006.01)
*A61B 17/32* (2006.01)
*A61B 17/34* (2006.01)

(52) U.S. Cl.
CPC ... *A61B 17/3211* (2013.01); *A61B 17/320036* (2013.01); *A61B 2017/320052* (2013.01); *A61B 2017/32096* (2013.01); *A61B 2017/3407* (2013.01)

(58) Field of Classification Search
CPC ........... A61B 2017/320052; A61B 17/320036; A61B 2017/32096
See application file for complete search history.

(56) References Cited

U.S. PATENT DOCUMENTS

| | | | | |
|---|---|---|---|---|
| 4,058,114 | A * | 11/1977 | Soldner | A61B 8/0833 600/461 |
| 4,638,799 | A * | 1/1987 | Moore | A61B 17/3403 604/116 |
| 4,733,661 | A * | 3/1988 | Palestrant | A61B 17/3403 128/DIG. 26 |
| 4,841,967 | A * | 6/1989 | Chang | A61B 17/3403 606/130 |
| 4,883,053 | A * | 11/1989 | Simon | A61B 17/3403 606/130 |
| 5,273,024 | A * | 12/1993 | Menon | A61B 17/3417 128/898 |
| 5,575,794 | A * | 11/1996 | Walus | A61B 6/12 403/293 |
| 5,893,861 | A | 4/1999 | Yumoto | |
| 5,911,707 | A * | 6/1999 | Wolvek | A61M 5/3287 128/DIG. 26 |
| 6,179,852 | B1 * | 1/2001 | Strickland | A61B 17/320036 606/167 |
| 6,283,942 | B1 * | 9/2001 | Staehlin | A61M 5/3287 604/116 |
| 7,635,336 | B1 * | 12/2009 | Pruter | A61B 8/0833 600/461 |
| 7,780,690 | B2 * | 8/2010 | Rehnke | A61B 1/313 600/104 |
| 7,909,815 | B2 * | 3/2011 | Whitmore | A61B 17/3403 606/1 |
| 8,216,185 | B2 * | 7/2012 | Berger | A61B 17/320036 604/164.01 |
| 8,273,098 | B2 * | 9/2012 | Strickland | A61B 17/320036 606/170 |
| 8,430,889 | B2 * | 4/2013 | Zeng | A61B 17/3403 606/1 |
| 8,608,765 | B1 | 12/2013 | Jurbala | |
| 8,672,960 | B2 * | 3/2014 | Briganti | A61B 17/320036 606/170 |
| 9,108,005 | B2 * | 8/2015 | Agee | A61B 17/320036 |
| 9,808,274 | B2 * | 11/2017 | Mirza | A61B 17/320036 |
| 2010/0069936 | A1 | 3/2010 | Palmer et al. | |
| 2013/0006240 | A1 | 1/2013 | McNally et al. | |
| 2013/0144318 | A1 | 6/2013 | Dinis Carmo et al. | |
| 2013/0231538 | A1 | 9/2013 | Guilford et al. | |
| 2014/0039533 | A1 | 2/2014 | Palmer et al. | |
| 2014/0290666 | A1 | 10/2014 | Agee et al. | |
| 2016/0113671 | A1 * | 4/2016 | Berger | A61B 17/0218 600/104 |

FOREIGN PATENT DOCUMENTS

| | | |
|---|---|---|
| JP | 2013-534166 | 9/2013 |
| JP | 2015-009137 | 1/2015 |
| WO | 1997010761 | 3/1997 |
| WO | 2010030872 | 3/2010 |
| WO | 2012023006 | 2/2012 |
| WO | 2012061738 | 5/2012 |

OTHER PUBLICATIONS

Extended European Search Reporting for related EP App No. 14908973.2 dated Jun. 8, 2018, 8 pgs.

* cited by examiner

SURGICAL INSTRUMENT FOR MAKING INCISIONS

CROSS-REFERENCE TO RELATED APPLICATIONS

This application is a U.S. National Stage entry of PCT Application No. PCT/JP2014/084150, filed on Dec. 24, 2014. The contents of the foregoing are incorporated by reference.

TECHNICAL FIELD

The present invention relates to a surgical instrument for performing incision and, in particular, to a surgical instrument for performing incision surgery that is used to perform tendon sheath incision surgery for stenotic tenosynovitis and aponeurectomy for Dupuytren's contracture.

BACKGROUND ART

The disease state of stenotic tenosynovitis (hereinafter also referred to as "trigger finger") is as follows: "A1 pulley," which is a ligamentous tendon sheath (hereinafter referred to as "tendon sheath") existing on the side of a matacarpophalangeal (MP) joint, which is a joint at the finger base, is thickened and finger flexor tendon (hereinafter referred to as "tendon") strangulation occurs, and thereby sliding of the tendon and tendon sheath is prevented and bending and stretching of the finger become difficult so as to cause pain.

To conduct surgical treatment, an A1 pulley that has been thickened is incised for improved tendon sliding in the major axis direction to release strangulation of the tendon. The release of the strangulation often leads to quick improvement in bending and stretching and reliving the pain.

In the conventional surgery for a trigger finger, the palm skin is incised approximately 2 cm. In general, while directly looking at the tendon and tendon sheath, open tendon sheath incision surgery is performed to incise the A1 pulley. Problems involved with this generally conducted surgery method include post-surgical symptoms, such as pain due to scarring of a tissue in the incised skin area, difficulty in clenching fingers, and restrictions of hand movement in daily life until a stitch is removed.

Dupuytren's contracture is a serious disorder in bending and stretching of a finger since a palm aponeurotic membrane under the skin of the palm and finger (hereinafter referred to as "aponeurotic membrane") is thickened and contracted, and the aponeurotic membrane is abnormally indurated and shortened.

The common surgery method for Dupuytren's contracture is aponeurectomy in which a substantial area of the palm and finger is incised to excise an abnormal aponeurotic membrane. In this method, however, the level of invasion is high, and there are problems such as the skill required for surgery and wound healing of the incised skin area.

As a measure for improving a relatively large incised skin area due to trigger finger surgery, a method called percutaneous surgery is used. In this method, minor skin incision of several millimeters is conducted, a dedicated surgical instrument, a single-use injection needle, or the like is inserted to blindly Incise an A1 pulley.

Also, for Dupuytren's contracture, there is another method called needle aponeurotomy that causes little invasion. To improve a finger bending and stretching disorder, this method is performed by blindly incising an abnormally indurated aponeurotic membrane under the skin using, e.g., a single-use syringe needle that has been pierced, from the palm. However, these types of surgery methods by blind operation involve a relatively high risk of injuring, by the needle, a tissue of a finger nerve, blood vessel, tendon, or the like.

A surgical instrument for use in the conventionally performed percutaneous tendon sheath incision surgery will now be described with reference to FIG. 11.

The tendon sheath incision blade shown in Patent Literature 1 can be used in both open surgery and percutaneous surgery. The tendon sheath incision blade includes a grip 101, a shaft 102 equipped on the grip, a blade portion 103 disposed on the side surface of the tip end portion of the shaft 102, and a guide portion 104 that extends in the direction from the lower section of the blade portion to the section toward which the blade portion protrudes. The blade disposed at the pointed end of the blade portion 103 is formed to have a circular arc shape in the area between the upper surface of the guide portion 104 and the upward inclining section of the blade portion 103. The sections above this circular arc-shaped upward inclining section of the blade, i.e., the middle and upper sections of the blade, are formed in a straight line so as to be in substantially parallel with the axial line direction of the shaft 102. The upper section of the blade portion 103 is formed in a step shape where the upper section protrudes from the side surface of the shaft 102.

This tendon sheath incision blade is inserted into the skin to incise the tendon sheath. When this tendon sheath incision blade is used in percutaneous surgery, the location of the tendon sheath cannot be confirmed directly and visually, and an incision blade without a blade portion to search for the entrance of the tendon sheath is prepared. After the entrance of the tendon sheath is searched for and the incision blade is in turn switched to one with a blade portion, an incision needs to be performed.

Another surgical instrument for use in percutaneous tendon sheath incision surgery will be described with reference to FIG. 12. The incision blade shown in Patent Literature 1, the tip end of a blade portion 105 to be inserted into the skin is thin, and has a special knife blade portion configured to incise a tendon so that the level of invention is low. A surgeon holding a handle portion 106 uses the surgeon's own sensation of hand and experience to blindly incise the tendon sheath. The surgeon thus needs to be practiced in use of the aforementioned incision blade.

CITATION LIST

Patent Literature

Patent Literature 1: Japanese Patent No. 3736877

Non-Patent Literature

Non-Patent Literature 1: Hiroshi Yasunaga, "Device of Experience-based Tendon Sheath Incision Blade for Trigger Finger," Orthopedics Additional 21, Nankodo Co., Ltd., published in 1992, p. 266-2.69.

SUMMARY OF INVENTION

Technical Problem

The aforementioned tendon sheath incision surgery and aponeurotomy using the respective surgical instruments or the like have been performed for a longtime, but have the following problems:

(1) In the conventional surgical treatment of a tendon sheath and aponeurotic membrane, skin and a subcutaneous tissue of the hand are incised to a certain width so that a sufficient view can be obtained by incision and the area to be treated can be directly viewed. Problems thus include post-surgical symptoms, such as pain and difficulty in clenching fingers due to scarring of a tissue in the incised skin area, and restrictions of hand movement in daily life until removal of a stitch.

(2) Percutaneous surgery performed by a certain group of people is a blind operation which largely depends on the experience and fingertip sensation of the surgeon when surgery is performed. During the surgical operation, there is a high risk that the surgical instrument used for incision erroneously damages a tissue of a tendon, nerve, blood vessel, or the like.

(3) For the existing percutaneous tendon sheath incision surgery, a surgical instrument having a guide structure is available. In this existing surgical instrument having a guide structure, a tool for insertion into the tendon sheath is provided with a blade for incising a tendon sheath. It is an essential surgical technique to accurately place a guide portion inside a tendon sheath and on the tendon surface. Due to percutaneous operation, however, there is a possibility that the guide portion penetrates too deep toward the tendon and that the tendon is thereby damaged by the blade portion. When a tendon sheath is thickened due to a disease and it is difficult to insert the guide portion into the tendon, there is a risk that the blade damages a nerve or blood vessel running in parallel with the tendon or the tendon sheath during an attempt to insert the surgical instrument into the tendon sheath. When the strangulated range of the tendon sheath to be incised is wide, sufficient improvement in triggering is not eventually achieved by one incision procedure. In this situation, the instrument needs to be again inserted blindly so as to reach a deeper site, which increases the risk of the procedure.

(4) To secure a view of the site subjected to the surgery, an assistant in addition to the surgeon and another surgical instrument are needed.

(5) As percutaneous surgery involves the aforementioned risks, performance of incision surgery requires an assistant and a surgical facility and environment. Accordingly, performance of surgery at a small medical institution is difficult, and facilities capable of performing the aforementioned surgery are limited.

The present invention has been made to solve the aforementioned problems. An object of the present invention is to provide a surgical instrument for performing incision whereby surgery can be safely and readily performed at a low level of invasion and the risk of damaging a tissue of a tendon, nerve, or blood vessel is minimum.

Solution to Problem

To solve the above object, the surgical instrument for performing incision according to the present invention includes: incised part reception means that is inserted into a body from a skin surface area near an area subjected to treatment that has been incised in advance and receives an incised part of a tendon sheath or aponeurotic membrane; guide fixture means that fixes the incised part reception means outside the body; and incision means that performs incision under guidance of the guide fixture means. The incision means is pressed onto the incised part reception means and moved to incise the tendon sheath or aponeurotic membrane.

By inserting the incised part reception means into the area below the lesion area of the tendon sheath or aponeurotic membrane and performing incision using the incision means under guidance of the guide fixture means, significant incision of skin or a subcutaneous tissue is not necessary.

The surgical instrument for performing incision according to the present invention further includes tissue perforation means that is inserted into the body from the skin surface area near the area subjected to treatment that has been incised in advance and form an insertion path to an area near a site to be treated. The incised part reception means is inserted into the insertion path formed by the tissue perforation means.

As the incised part reception means is inserted into the site to be treated after the insertion path is formed in advance by the tissue perforation means, a nerve or blood vessel running nearby is not damaged.

The surgical instrument for performing incision according to the present invention further includes incision means hold means that holds the incision means.

As the incision means hold means is included and the incision means hold moans can be thereby grasped to exert a sufficient force on the incision means, the to ado a sheath and aponeurotic membrane can be readily incised.

In the surgical instrument for performing incision according to the present invention, the incised part reception means includes a handle portion at one end and an incision table portion with a guide groove running in a longitudinal direction at the other end. The guide fixture means includes a base portion and an arm portion that extends from the base portion. The arm portion includes a slit that corresponds to the guide groove of the incised part reception means. The incision means is inserted from the slit of the guide fixture means and pressed onto the guide groove of the incised part reception means so as to run along the guide groove and the slit.

By provision of the foregoing configuration, the incised area is small, and incision can be stably performed so that the incision means does not deviate.

The surgical instrument for performing incision according to the present invention further includes a recessed portion at a tip end of the guide groove of the incision table portion of the incised part reception means.

As the recessed portion is provided at the tip end of the guide groove of the incision table portion, the surgeon can know that the incision is completed by feeling the sense of the tip end of the incision means failing into the recessed portion. As a result, the risk of injury of a tissue of a tendon, nerve, blood vessel, or the like near the treated site can be significantly decreased.

In the surgical instrument for performing incision according to the present invention, the base portion of the guide fixture means is configured to hold and fix the handle port ion of the incised part reception means.

The site to be treated can be thereby firmly held by the incised part reception means and the guide fixture means so as to stably conduct incision surgery.

In the surgical instrument for performing incision according to the present invention, a scale is provided on the handle portion of the incised part reception means, and another scale is provided on the arm portion of the guide fixture means so that the scales are synchronized with each other to identify a location of the incision table portion of the incised part reception means fixed to the guide fixture means.

As these scales are provided, the location of the incised part reception means relative to the guide fixture means can be confirmed. Consequently, the relative relation of the site to be treated to the guide fixture means and the incised part reception means can be understood, which ensures the accuracy of surgery.

The surgical instrument for performing incision according to the present invention includes a downwardly protruding support column portion at the other end of the arm portion that extends from the base portion of the guide fixture means. An escape space is formed below the arm portion between the base portion and the support column portion.

The arm portion is thereby placed separately from the skin when the guide fixture means is disposed. The surgeon can readily observe the incision means puncturing into the skin through the slit. As the skin and subcutaneous tissue in a thinned portion can be readily moved, the range where the incision means can move in each skin puncture can be widened.

In the surgical instrument for performing incision according to the present invention, the tissue perforation means includes a handle portion at one end and an insertion portion at the other end. The insertion portion has a sharp tip end portion and an expansion portion whose width is greater than that of the tip end portion. Also, the insertion portion bends smoothly toward the handle portion, and a bottom surface portion of the insertion portion is in a circular arc shape.

Since the insertion portion smoothly bends from the tip end portion to the handle portion and the bottom surface portion is in a circular arc shape, the insertion portion can be inserted inside the synovial tendon sheath in parallel with the tendon without damaging the tendon surface, etc. As the expansion portion is provided next to the tip end portion up to the handle portion, an insertion path of the incised part reception means can be formed while the level of insertion of the tissue perforation means can be confirmed on the basis of the feeling of pressure applied to the tip end portion and the expansion portion. The path to the target site can be formed without puncturing too deep into the living body.

In the surgical instrument for performing incision according to the present invention, the incision means hold means includes: an axis portion including an engagement portion on which the incision means is mounted to hold the same; a main body portion that fixes or swingably supports the axis portion; and fasten means that loosely fastens the axis portion to the main body portion.

When the incision means is mounted on the axis portion for use, incision can be readily performed as a sufficient force can be exerted on the incision means. Since the incision means can use a single-use syringe needle that can be replaced for use, incision can be performed with the incision performance that is always at a preferable level. As the fasten means is provided, by loosening the fasten means to make the axis portion swingable, the incision means can be readily mounted on the engagement portion.

Advantageous Effects of Invention (1) The surgical instrument for performing incision according to the present invention produces the below-mentioned advantageous effects. Unlike the conventional blind percutaneous surgery, surgery does not largely depend on intuition and experience. Even though the instrument is used in surgery, a tissue other than the incised part is not damaged. The instrument can be provided as an instrument that ensures performance of accurate surgery. Advantageous effects of the present invention are hereinbelow described in detail.

A tendon sheath and aponeurotic membrane can be incised without significantly incising skin or a subcutaneous tissue, and surgery with very little invasion can be achieved. Post-surgery damage, such as scarring of skin or a subcutaneous tissue, can be thereby reduced to a minimum. In other words, post-surgery skin suturing is not necessary in many cases. Suture wound management up to the time of stitch removal contributes to decreasing restrictions on movements in daily life and to enhancing the quality of life of the patient.

In the conventional open surgery, the skin is incised approximately 1.5 to 2 cm. However, in the method using the surgical instrument for performing incision according to the present invention, the skin incision is very small at approximately 2 mm. As the skin incision is small, stitching is not necessary. The skin simply needs to be bonded using an instantaneous adhesive for medical use or a sterilization tape for surgical use. The time period up to removing gauze in the method of using the surgical instrument for performing incision according to the present invention is approximately three to ten days, which is less than ⅓ that of the conventional open surgery.

(2) The incised part reception means inserted as an incision guide into the body, the incision means that incises a tendon sheath and an aponeurotic membrane, and the guide fixture means that is disposed outside the body to restrict the moving range of the incision means for incision are combined. The foregoing structure eliminates the possibility of damaging an important tissue around the diseased area and ensures the safety of surrounding tissues that has not been adequately addressed by the conventional percutaneous surgery.

(3) Unlike the existing dedicated surgical instrument, when percutaneously incising a tendon sheath in a trigger finger, an incised part reception means to be inserted into a tendon sheath can be safely inserted into the tendon sheath as a guide without damaging the tendon and a surrounding tissue thereof since the incised part reception means does not have a blade. A skin incision part serving as an insertion area for incising a tendon sheath can be incised without a structural problem even when the skin incision part is somewhat far from the diseased site. In the event that, e.g., stenosing of a tendon sheath has been spread to a wide range or releasing strangulation is not sufficient in one occasion of tendon sheath incision surgery, the tendon sheath can be safely incised.

(4) The conventional open surgery requires an assistant in addition to the surgeon and another instrument to secure a view of the surgical site. However, use of the surgical instrument for performing incision according to the present invention enables surgical operation to be performed by one surgeon.

(5) Since preparation of the facility and environment for surgery is readily made, introduction at a small-sized medical facility, such as a clinic, is possible.

DESCRIPTION OF EMBODIMENTS

Embodiments of the present invention will now be described in detail with reference to the attached drawings.

Embodiment 1

Embodiment 1 will be described on the basis of an example of using a surgical instrument for performing incision 1 according to the present invention for a trigger finger.

Figure 1:
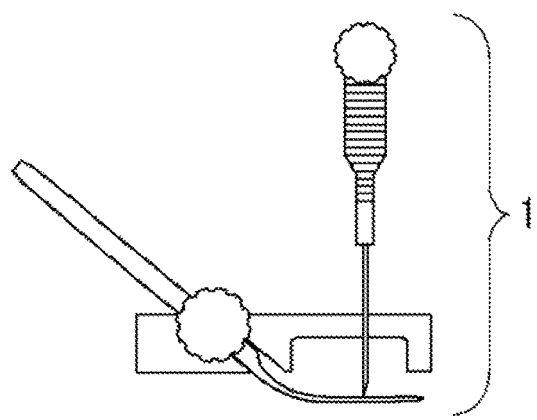
FIG. 1 is a schematic side view illustrating a use situation of a surgical instrument for performing incision according to Embodiment 1 of the present invention.
Figure 2:
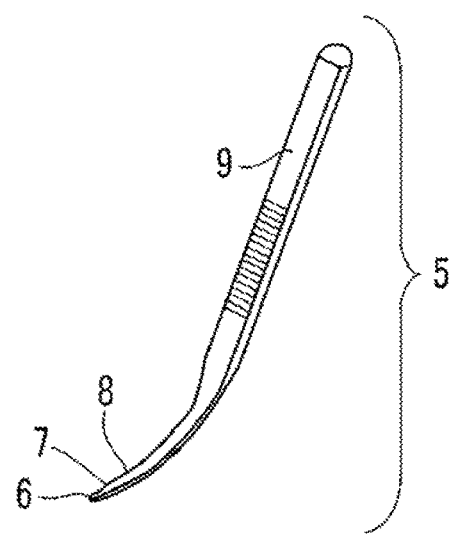
FIG. 2 is a perspective view of tissue perforation means of the surgical instrument for performing incision according to the present invention.
Figure 3:
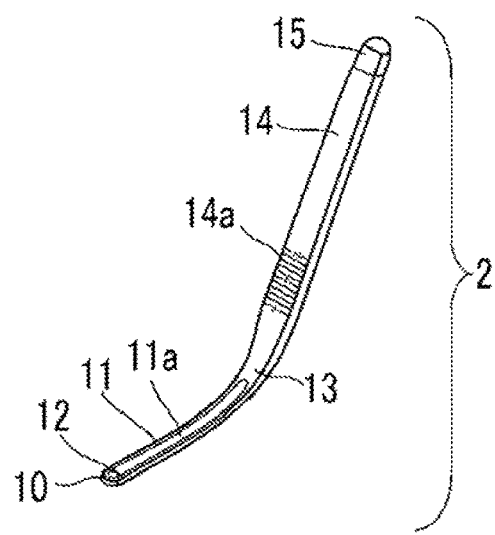
FIG. 3 is a perspective view of incised part reception means of the surgical instrument for performing incision according to the present invention.
Figure 4:
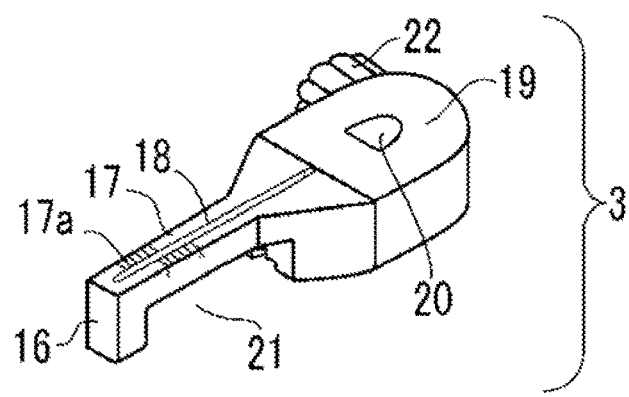
FIG. 4 is a perspective view of guide fixture means of the surgical instrument for performing incision according to the present invention.
Figure 5:
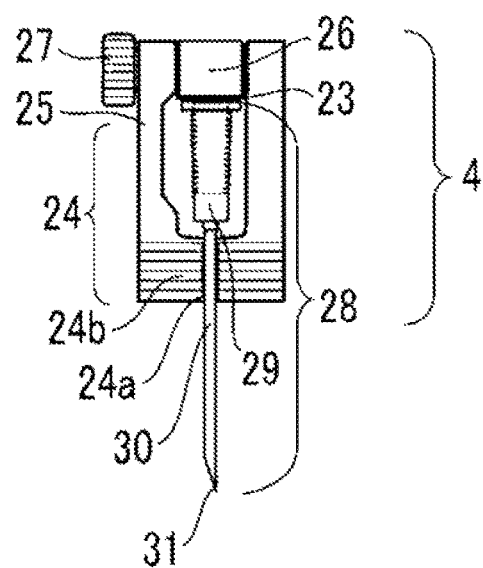
FIG. 5 is a front view illustrating incision means engaged with incision means hold means of the surgical instrument for performing incision according to the present invention.
Figure 6:
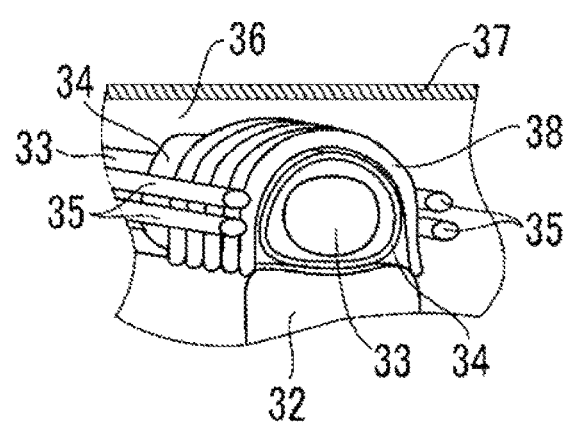
FIG. 6 is an illustrative disease state diagram illustrating a method of using the tissue perforation means illustrated in FIG. 2 according to the present invention.
Figure 7:
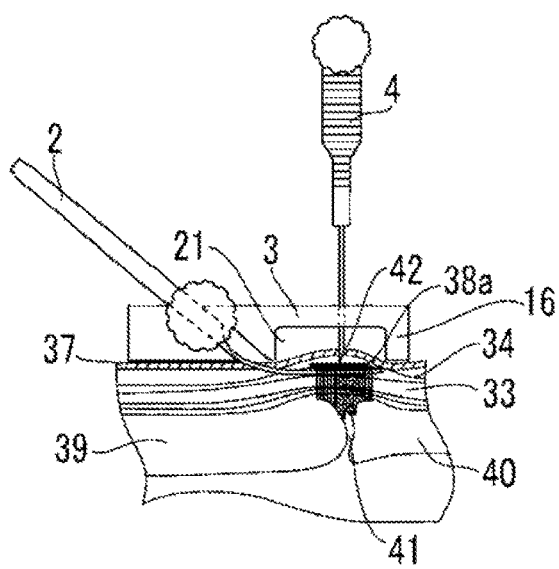
FIG. 7 is a schematic cross-sectional view illustrating an example use of the surgical instrument for performing incision according to the present invention.
Figure 8:
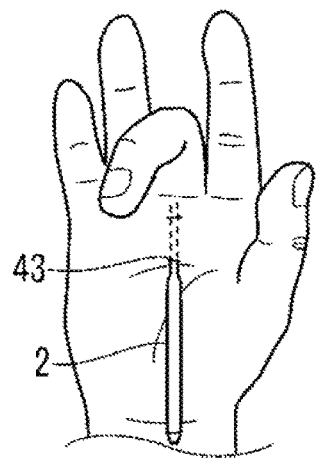
FIG. 8 is an illustrative disease state diagram illustrating a location on a palm surface incised by the surgical instrument for performing incision according to the present invention.

FIG. 1 is a schematic side view illustrating a use situation of a surgical instrument for performing incision according to Embodiment 1 of the present invention. FIG. 2 is a perspective view of tissue perforation means of the surgical instrument for performing incision. FIG. 3 is a perspective view of incised part reception means of the surgical instrument for performing incision. FIG. 4 is a perspective view of guide fixture means of the surgical instrument for performing incision. FIG. 5 is a front view illustrating incision means engaged with incision means hold means of the surgical instrument for performing incision. FIG. 6 is an illustrative disease state diagram illustrating a method of using the tissue perforation means illustrated in FIG. 2. FIG. 7 is a schematic cross-sectional view illustrating a use example of the surgical instrument for performing incision. FIG. 8 is an illustrative disease state diagram illustrating a location on a palm surface incised by the surgical instrument for performing incision.

The surgical instrument for performing incision 1 according to the present invention illustrated in FIG. 1 includes: incised part reception means 2 illustrated in FIG. 3; guide fixture means 3 illustrated in FIG. 4, which acts as a guide that holds and fixes the incised part reception means 2 and restricts the incision range; and incision means that incises a tendon sheath under guidance of the guide fixture means 3. The surgical instrument for performing incision 1 is inserted into a ligament tendon sheath 38 (hereinafter referred to as "tendon sheath"), which is the treatment target illustrated in FIG. 6, and has a guide feature that is fixed inside an A1 pulley 38a or the tendon sheath, as illustrated in FIG. 7, and thereby indicates the location of the tendon sheath and supports the tendon sheath. The guide fixture means 3 is provided with a slit 18 to allow incision means 28 to be inserted as illustrated in FIG. 5.

Here, the slit 18 is provided as a guide feature of the guide fixture means 3, but an element other than the slit 18 whose shape is different from that of the slit 18 may be used as long as the incision means can be thereby stabilized to incise a tendon sheath, etc. An example configuration may be where a recess is formed and one side surface can be used as a ruler. Here, a description will be given on the basis of the configuration where incision means hold means 4 equipped with the incision means 28 is included. Further, a description will be given by referring to the configuration of using tissue perforation means 5 (see FIG. 2) that forms a surgical path for inserting the incised part reception means 2 into the tendon sheath 38.

FIG. 2 illustrates the tissue perforation means 5. In FIG. 2, a tip end portion 6 is inserted from a skin incision part 43 (see FIG. 8) that has been, incised in advance. The tissue perforation means 5 is configured by an expansion portion 7 that expands a perforation portion of the synovial tendon sheath after the tip end portion 6 having a relatively thin tip end to be used to perforate a synovial tendon sheath is completely inserted into the synovial tendon sheath, and a parallel portion 8 that has the tip end portion 6 and the expansion portion 7 as its tip end area, wherein the section consists of these portions is in a rounded rectangular cylinder shape so as not to damage a surrounding tissue. The parallel portion 8 is bent in an R shape toward a handle portion 9.

In this surgery, after the synovial tendon sheath 34 that exists around the finger flexor tendon 33 (hereinafter simply referred to as "tendon") illustrated in FIG. 6 is perforated by the tip end portion 6, the parallel portion 8 can be inserted through the use of the bend of the bottom portion. This structure prevents the surface of the tendon 33 from being damaged as the tip end portion 6 is inserted inside the synovial tendon sheath 34 in parallel with the tendon 33. The handle portion 9 is connected with the parallel portion 8 and has a circular cross section with its top surface cut-off. As the top surface is cut-off, the surgeon can readily hold the handle portion 9 and can recognize the pointing direction of the tip end portion 6 after the parallel portion 8 is inserted inside the synovial tendon sheath 34.

FIG. 3 illustrates the incised part reception means 2. A tip end portion 10 of the incised part reception means 2 has a pointed end which is blunt compared with that of the tip end portion 6 of the tissue perforation means 5, whereby when inserted into the living body, a tissue is unlikely to be damaged. An incision table portion 11 where the tip end portion 10 is formed is designed so that the width thereof is slightly smaller than that of the insertion portion 8 of the tissue perforation means 5, whereby the incision table portion 11 can be smoothly inserted into a surgical path formed by the tissue perforation means 5. A shallow guide groove 11a is formed on the upper surface of the incision table portion 11. To perform incision, the tip end of the incision means used for incision is allowed to move along the inner side of the guide groove 11a.

A recessed portion 12 formed on the pointed end side of the guide groove 11a is recessed deeper than the guide groove 11a. The surgeon is caused thereby to recognize that the incision means running through the guide groove 11a has reached the furthest pointed end of the guide groove 11*a*. A bent portion 13 is bent in an R-shape as the parallel portion 8 of the tissue perforation means 5 is. A handle portion 14 is configured to be connected with the incision table portion 11 through the bent portion 13 and shorter than the handle portion 9 of the tissue perforation means 5. This configuration makes it difficult to strongly grasp the handle portion 14. On the upper surface of the handle portion 14, a scale 14*a* is inscribed. When connected with and held by the guide fixture means 3 illustrated in FIG. 4, it is possible to visually understand how deep the tip end portion 10 of the incised part reception means 2 is inserted below the skin. A base end portion 15 is squeezed to be angled so as to be readily coupled to the guide fixture means 3.

The incised part reception means 2 is a surgical instrument for insertion from the skin incision part, whose location is the same as that of the tissue perforation means 5, to a surgical path secured by the tissue perforation means 5. The bent angle of the incised part reception means 2 is the same as that of the tissue perforation means 5 and the incised part reception means 2 can be operated by the same operation as the tissue perforation means 5. The incised part reception means 2 with a plurality of lengths are prepared, so that surgery can be performed at different surgical instrument lengths depending on the distance between the skin incision part and the tendon sheath or aponeurotic membrane to be incised.

FIG. 4 illustrates the guide fixture means 3. An arm portion 17 has a support column 16 at its tip end section and extends from a base portion 19. The base portion 19 is configured to have a sufficient bottom area which is not too large to disturb surgery and prevents the guide fixture means 3 from being unstable. An oblique hole portion 20 is an oblique hole formed to penetrate through the base portion 19 from its top to bottom surfaces. The base end portion 15 of the handle portion 14 of the incised part reception means 2 is inserted into a lower-side opening thereof so as to be slid and held at a predetermined position. A knurled knob 22 is configured to fix the handle portion 14 of the incised part reception means 2 that has been inserted into the oblique hole portion 20. The knurled knob 22 is fastened so that the tip end thereof is in pressure contact with the handle portion 14 of the incised part reception means 2 for fixing and holding the handle portion 14.

Here, the arm portion 17 is configured to be located directly above the incision table portion 11 of the incised part reception means 2 when the incised part reception means 2 is fixed to and held by the base portion 19, and the slit 18 is formed in the longitudinal direction thereof. As illustrated in FIG. 5, the slit 18 is configured as a long hole whose width is slightly wider than the incision means 28 for incision. The slit 18 is located directly above the guide groove 11*a* of the incised part reception means 2 when the incised part reception means 2 is fixed to and held by the base portion 19.

At the same time when the incision means 28 is made movable smoothly in the slit 18, the width of the arm portion 17 prevents the incision means 28 from being oriented toward the direction other than, the slit 18. By virtue of this configuration, when the incised part reception means 2 is combined with the guide fixture means 3, the incision means 28 that has been inserted from the upper side of the slit 18 does not deviate sidewards from the incised part reception means 2. The scale 17*a* is formed along the slit 18 on the upper surface of the arm portion 17 and is moved in synchronization with the scale 14*a* that is formed on the handle portion 14 of the incised part reception means 2.

Also, the scale 17*a* is configured to indicate the subcutaneous location of the tip end of the incision table portion 11 of the incised part reception means 2 that is fixed to and held by the base portion 19.

As illustrated in FIG. 7, the support column 16, which is at the tip end of the arm portion 17, is a portion that is in contact with the skin. As the support column 16 has a sufficiently large bottom surface area, the support column 16 contributes to the stability of the guide fixture means 3. The support column 16 also has the feature for guiding the incision table portion 11 of the incised part reception means 2 so that its tip end does not penetrate too deep into the living body. In addition, a thinned portion 21 that acts as an escape space from the skin contact surface is formed between the support column 16 and the base portion 19. As the arm portion 17 is disposed separately from the skin when the guide fixture means 3 is disposed, the thinned portion 21 allows the surgeon to readily observe the incision means 28 that has been inserted, through the slit 18 and punctured into skin 37. Also, as the ease of the movement of the skin 37 and a subcutaneous tissue 36 increases, the thinned portion 21 contributes to widening the range where the incision means 28 can move in one occasion of skin puncturing.

FIG. 5 illustrates the situation where the incision means hold means 4 is engaged with the incision means 28. In this situation, an engagement portion 23 uses, as the incision means 28, a single-use syringe needle for general medical equipment for a management purpose. The engagement portion 23, which has a standard angle to be engaged with a needle base 29 of the incision means 28, is formed integrally with an axis portion 26. An arm portion 25 fixes and holds the axis portion 26. Also, the arm portion 25 has in its upper left section a through hole through which a stripper bolt 27 passes and has in its upper right section a female thread which runs in parallel with the through hole and where a screw 27 is fastened. When the axis portion 26 is allowed to pass therethrough and the stripper bolt 27 is fastened, the arm portion 25 fixes and holds the axis portion 26. When the stripper bolt 27 is fastened at the upper left and right portions of a main body portion 25, deflection occurs from, these portions to the central portion. By reducing the volume of the left side where the through hole exists, the deflection of the left side with the through hole increases, and the right side with the female thread is stabilized. Thus, this configuration is made such that a male thread portion of the stripper bolt 27 is strongly fastened. FIG. 5 illustrates a configuration for a right hander. In the configuration for a left hander, the left and right and the top and bottom are reversed so that the stripper bolt 27 is fastened from the right side.

A grip portion 24 is formed with thinning the end portion side of the arm portion 25. In the middle, a groove 24*a* whose diameter is slightly greater than that of a needle tube 30 of the incision means 28 is formed. The configuration is made such that the grip force of the incision means 28 is increased by engaging with the needle tube 30 of the incision means 28 for incision. A knurling 24*b* that acts as an antiskid part when being gripped is provided, and, while in use, gripping from both surfaces or a side surface by fingers is possible.

On the basis of the above-described configurations, a use method and advantageous effect of the surgical instrument for performing incision 1 will now be described. First of all, with reference to FIGS. 6 and 7, the disease state of a trigger finger will be explained according to Embodiment 1. The subcutaneous structure of the palm and finger is hereinbelow described. In the deepest layer, there exist bones 32, such as a metacarpal bone 39 and a coxal bone 40, and a joint. On the palm side thereof, the tendon 33 and the synovial tendon sheath 34 exist. There exists nerves and blood vessels 35 for maintaining the sense and blood flow of the finger on both sides of the tendon 33. In a shallower layer, the subcutaneous tissue 36 exists. In the outermost layer, the skin 37 exists. The subcutaneous tissue 36 consists mainly of a fat tissue and acts as a pad for grasping an article by the fingers or palm. In the subcutaneous tissue 36, an aponeurotic membrane 44 (see FIG. 9) that is a connective tissue with a suitable level of elasticity and tensile strength exists. The subcutaneous tissue 36 contributes to maintaining the palm shape.

The tendon 33 is in contact with an MP joint 41, which exists between the metacarpal bone 39 and the coxal bone 40, and runs through the palm side thereof in the longitudinal direction. As the tendon 33 is pulled by a muscle in the central direction, the finger is automatically bent. The circumference of the tendon 33 is almost entirely covered by the soft and bag-shaped synovial tendon sheath 34. The synovial tendon sheath 34 is filled with a small amount of synovial fluid, whereby the finger can smoothly move. On the palm side of the MP joint 41, there exist the synovial tendon sheath 34 and the A1 pulley 38a, which is one of the tendon sheaths 38 that are relatively hard and strong connective tissues. The A1 pulley 38a is considered to be a tissue intended for fixing the tendon 33 to a tissue of the bone 32, the MP joint 41, etc. Due to anatomical features, absence of the tendon sheath 38 does not hinder bending and stretching of a human finger. On the further palm side of the synovial tendon sheath 34 and the A1 pulley 38a, which surround the tendon 33, the subcutaneous tissue 36 of the palm, consisting mainly of a fat and connective tissue exists.

In the disease state of a trigger finger, the tendon sheath 38 is pathologically thickened to strangulate the tendon 33, whereby smooth movement of the tendon 33 and the tendon sheath 38 is hindered. Accordingly, bending and stretching of the finger become difficult, and the finger is pained.

When conducting operative treatment, in order to improve slide of the tendon 33, the tendon sheath 38 that has been thickened is incised in the longitudinal direction to release strangulation of the tendon 33. As illustrated in FIG. 8, the tendon sheath 38 is normally incised in the palm center. Upon completion of incision, the tendon sheath 38 may be left unattended. By releasing strangulation, the bending and stretching and the pain of the finger are likely to be improved quickly.

In turn, the operation for tendon sheath incision surgery of an actual trigger finger according to Embodiment 1 will be described. Firstly, the tissue perforation means 5 is used to form an insertion path for the incised part reception means 2. The tissue perforation means 5 is inserted from the skin incision part 43, which has been incised about 2 mm in advance in an area approximately 2 cm from the tendon sheath 38 to be incised. Into the synovial tendon sheath 34, which is closer to the surface layer than the tendon 33 is, the tissue perforation means 5 is inserted in the longitudinal direction. The tip end of the tissue perforation means 5 is not a simple taper shape, but the width, increases from the tip end portion 6 to the expansion portion 7. The tissue perforation means 5 can safely perform at one time two types of operation for the synovial tendon sheath 34: perforation and expansion. The area directly above the tendon sheath to be incised is normally incised approximately 2 mm. A mosquito forceps or the like is inserted to bluntly separate the area directly above the tendon sheath.

The tip end portion 6 for performing perforation in the synovial tendon sheath 34 is designed to be relatively thin and can perform perforation in the synovial tendon sheath 34 with a small level of resistance. After the tip end portion 6 is entirely inserted in the synovial tendon sheath 34, the expansion portion 7 expands the perforation portion in the synovial tendon sheath 34. As the tip end portion 6 is in the synovial tendon sheath 34 during expansion, the tissue perforation means 5 is not fallen from inside the synovial tendon sheath 34 even with a strong force applied for the sake of expansion.

When a surgeon performs puncture of the synovial tendon sheath 34 by the tip end portion 6, the surgeon feels resistance by the surgeon's own finger. After the tip end portion 6 is completely inserted inside the synovial tendon sheath 34, no resistance acts for the moment. When the tissue perforation means 5 is further inserted to expand the area inside the synovial, tendon sheath 34 by the expansion portion 7, an increase in the resistance can be felt again. After expansion is sufficiently performed and the parallel portion 8 is pierced into the synovial tendon sheath 34, absence of resistance can be felt again. By feeling a resistance increase and decrease during expansion of the perforation portion during the procedure, the surgeon can confirm each phase of puncture and expansion of the synovial tendon sheath 34.

By performing operation using the bend formed at the tip end after the parallel portion 8 perforates the synovial tendon sheath 34, the tip end portion 6 is inserted inside the synovial tendon sheath 34 in parallel with the tendon 33, and damage to the surface of the tendon 33 can be avoided. The upper surface of the tissue perforation means 5 between the tip end portion 6 and the insertion portion 8 is a flat surface that preferably reflects an ultrasonic wave. In the series of procedures, an ultrasonic diagnostic device can be used during the surgery to confirm the positional relationship between a tissue of the tendon 33, the synovial tendon sheath 34, etc, and the tissue perforation means 5, and surgery can thus be more safely performed. A sufficient surgical path for inserting the incised part reception means 2 into the synovial tendon sheath 34 can thereby be formed.

The incised part reception means 2 is inserted into the insertion path of the incised part reception means formed as described above. The incised part reception means 2 is inserted into the body from the tip end portion 10. Compared with the tissue perforation means 5, the pointed end is in a blunt shape, and damage to a tissue during insertion into the living body is not likely to occur. The incised part reception means 2 thus inserted is used to confirm in an ultrasonic test short-axis image whether the incision table portion 11 is disposed in contact with the palm surface layer of the tendon 33. Also, by checking the recessed portion 12 of the incised part reception means 2 in the ultrasonic long-axis image, the range of the tendon sheath 38 to be incised can be confirmed prior to incision.

The incised part reception means 2 has been inserted from the skin incision part 43 into the synovial tendon sheath 34, which is closer to the surface layer than the tendon 33 is. Without extracting the incised part reception means 2 from inside synovial tendon sheath 34, the surgeon uses the drawing angle of the base end portion 15 to insert the incised part reception means 2 to the oblique hole portion 20 of the guide fixture means 3 from the bottom surface side thereof to slide the incised part reception means 2. The guide fixture means 3 is slid, against the incised part reception means 2 and disposed on the palm until the guide fixture means 3 is in a state where the guide fixture means 3 is settled on the palm. The incised part reception means 2 is directly connected with the oblique hole portion 20 of the guide fixture means 3, After connection therebetween, the arm portion 17 of the guide fixture means 3 and the slit 18 provided to the arm portion 17 are located directly above the incision table portion 11 of the incised part reception means 2.

In this situation, the handle portion 14 of the incised part reception means 2 is raised toward the palm side while keeping the incision table portion 11 of the incised part reception means 2 parallel. When the tendon sheath 38 is pulled, toward the side of the skin 37, the incised part reception means 2 and the guide fixture means 3 are fixed. The foregoing fixation is made by fastening the knurled knob 22. By fixing the incised part reception means 2 and the guide fixture means 3, the incision table portion 11 of the incised part reception means 2, the bottom surface of the base portion 19 of the guide fixture means 3, and the bottom surface of the support column 16 of the guide fixture means 3 hold therebetween the tendon sheath 38 and the skin 37 of the patient. Accordingly, the guide fixture means 3 and the incised part reception means 2 are stably fixed. By raising the incised part reception means 2, at the location in the synovial tendon sheath 34 closest to the palm side, the incision table portion 11 of the incised part reception means 2 is fixed directly above the tendon 33.

In this time, by looking at the scale 17*a* on the upper surface of the arm portion 17 of the guide fixture means 3, the surgeon can recognize the location of the recessed portion 12 of the incised part reception means 2. Specifically, the scale 17*a* on the upper surface of the arm portion 17 of the guide fixture means 3 is synchronized with the scale 14*a* of the incised part reception means 2. The scale 14*a* inscribed on the upper surface of the handle portion 14 of the incised part reception means 2 indicates the under-skin depth of the incision table portion 11 of the incised part reception means 2 with respect to the height of the upper surface of the oblique hole portion 20 of the guide fixture means 3. When the reading of the scale 14*a* on the upper surface of the incised part reception means 2 is 2 mm under the skin, the recessed portion 12 of the incised part reception means 2 exists directly below the location where the reading of the scale 17*a* on the upper surface of the arm portion 17 is 2 mm. The confirmation by the surgeon of the range of the tendon sheath 38 to be subcutaneously incised can be facilitated.

As described above, incision of the tendon sheath 38 is initiated after the incised part reception means 2 and the guide fixture means 3 are disposed and fixed on the surface of the skin 37 that is near the area subjected to treatment.

Prior to the above, the incision means 28 is engaged with the engagement portion 23 of the incision means hold means 4 so that the incision means 28 can be readily grasped in advance. In this situation, the surgeon can loosen the stripper bolt 27 and rotate the axis portion 26 relative to the arm portion 25 so as to change the location of the engagement portion 23, whereby the incision means 28 can be readily engaged with the engagement portion 23. Simultaneously, the surgeon engages the incision means 28 with the engagement portion 23 so that the cut surface of a tip end 31 of the incision means 28 is oriented toward a direction where incision can be readily performed.

The incision means 28 set as described above is used to rotate the axis portion 26 relative to the arm portion 25, to fasten the needle tube 30 by the stripper bolt 27 so that the needle tube 30 is engaged with a groove 24*a* in front of the grip portion 24, and to fix the needle tube 30 to the incision means hold, means 4.

In turn, the tip end 31 of the incision means 28 fixed to the incision means hold means 4 is inserted from the upper section of the slit 18 of the guide fixture means 3. In a skin puncture part 42, which has been determined as the target incision location on the basis of an anatomical observation from outside the body, the tip end 31 is proceeded by penetrating through the skin 37 and the subcutaneous tissue 36 until being in contact with the tendon sheath 38. In this situation, on the other side of the tendon sheath 38, the incision table portion 11 of the incised part reception means 2 exists. The tip end 31 of the incision means 28 is guided by the slit 18 of the guide fixture means 3 and received by the guide groove 11*a* of the incision table portion 11. Accordingly, damage to the tendon 33 can be prevented when the incision means 28 punctures.

Under the above situation, the tip end 31 of the incision means 28 is pressed onto the guide groove 11*a* so that the incision means 28 moves, to incise the tendon sheath 38. Specifically, the tip end of the incision means 28 is pressed onto the guide groove 11*a* so that the incision means 28 moves along the guide groove 11*a* and the slit 18 directly thereabove, to incise the tendon sheath 38. The incision means 28 is thereby guided by both the guide groove 11*a* and the slit 18, so that the incision means 28 is not deviate to left and right while moving. Also, the tip end portion of the guide groove 11*a* is provided with the recessed portion 12. While the incision means 28 is moved along the guide groove 11*a*, the tip end of the incision means 28 falls into the recessed portion 12. Thereby, the surgeon can acknowledge that incision has been completed by feeling the impact of the fall, and, more importantly, it is possible to prevent an unnecessary portion from being incised by further moving the incision means 28.

As described above, using the three means, i.e., the incised part, reception means 2, the guide fixture means 3, and the incision means 28, the location of a diseased area where incision is needed can be determined by the instrument. By moving the incision means 28 along the slit 18 provided on the guide fixture means 3, a procedure can be performed, unlike a blind operation depending on intuition or experience. As a result, the surgical instrument for incision according to the present invention enables accurate incision of the tendon sheath 38 and the aponeurotic membrane 44 without damaging a tissue, such as the nerve and blood vessel 35 near the tendon sheath 38. As accurate incision is made possible, a large scale incision of the skin 37 or the subcutaneous tissue 36 is not necessary, and surgery with extremely small invasion is realized. Post-surgery damage, such as scarring of skin or a subcutaneous tissue, can be reduced to a minimum.

In the guide fixture means 3, the thinned portion 21 is formed in the lower section of the arm portion 17 where the slit 18 is provided. The tendon sheath 38 can be incised while directly looking at the skin puncture part 42 for the incision means 28 inserted into the slit 18 of the guide fixture means 3. Incision surgery can be readily performed with a sense of security.

As the incision means 28 is mounted on the incision means hold means 4 for use, a sufficient force can be exerted on the incision means 28 during incision, and accurate incision can be readily performed. Since the incision means 28 can be removably mounted on the engagement portion 23 of the axis portion 26, by using the incision means 28 as a replaceable single-use instrument, incision can be always performed at a preferable performance level. In addition, by loosening the stripper bolt 27 so that the axis portion 26 is swingable, the incision means 28 can be readily mounted on the engagement portion 23.

Embodiment 2

Another example of the present invention will now be described in detail with reference to the attached drawings. In Embodiment 2, another example of the surgical instrument for performing incision 1 according to the present Invention for Dupuytren's contracture will be described.

Figure 9:
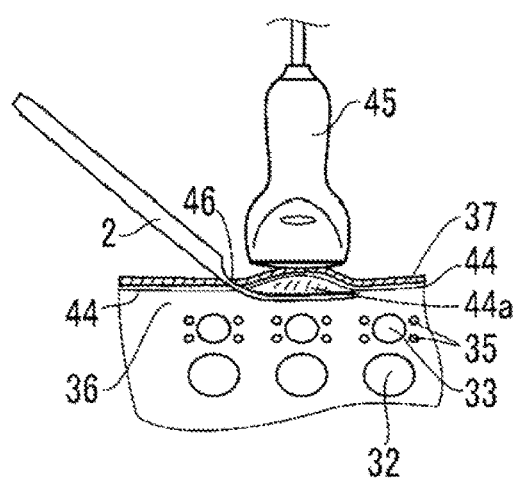
FIG. 9 is an illustrative disease state diagram illustrating a method of using a surgical instrument for performing incision according to Embodiment 2 of the present invention.

First of all, FIG. 9 is an illustrative disease state diagram illustrating a method of using the surgical instrument for performing incision 1 according to Embodiment 2 of the present invention.

On the basis of the configuration of the aforementioned surgical instrument for performing incision 1, a method of using the aforementioned surgical, instrument and an advantageous effect thereof according to another example will be described.

First of all, with reference to FIG. 9, the disease state of Dupuytren's contracture in Embodiment 2 will be described. Dupuytren's contracture is a disease whose cause is unknown and which causes abnormal fibrous thickening and contraction of a palmar aponeurotic membrane 44 (hereinafter referred to as "aponeurotic membrane") and flexion contracture of a finger. In many cases, Dupuytren's contracture occurs as a subcutaneous induration disease near a distal palmar crease on the ring, little, or middle finger palm. Induration of the aponeurotic membrane 44 progresses gradually to the area under the skin of the finger PIP joint, simultaneously with contraction of the aponeurotic membrane 44. The thickened and contracted condition of a pathogenic aponeurotic membrane 44a can be felt on the body surface as a restiform body extending in the main axis under the skin. When the induration is left unattended and the symptom progresses, the fingers cannot be extended and can be clenched only in the posture illustrated in FIG. 10. As the finger that cannot be extended is an obstacle, the function of the entire damaged hand deteriorates.

Types of surgery in which operative treatment is performed can be roughly divided into the following two types: 1) the thickened aponeurotic membrane 44 is excised as invasively as possible; and 2) only the site where the aponeurotic membrane 44 stretches like a rope and which is responsible for restricting finger extension is incised percutaneously. In the latter type of surgery, after sensing the aponeurotic membrane 44 stretching under the skin in the palm portion in the major axis direction, a single-use syringe needle, etc. subcutaneously punctures, and the tip of the single-use syringe needle, etc. is used to incise the fiber of the aponeurotic membrane 44, to release flexion contracture of the finger. The main disadvantage of the former type 1) is that subcutaneous treatment is required in a wide area ranging from the palm to the finger and the level of invasion is high. The main disadvantage of the latter type 2) is that as the nerve and blood vessel 35 and the tendon 33 run in a layer deeper than the aponeurotic membrane 44, there is a risk that the needle tip can cause damage due to blind operation.

Clinically speaking, the type of surgery conducted for Dupuytren's contracture is determined considering, inter alia, the movable range of the finger and restrictions on the patient's life, and patient's choice. The latter method of percutaneously releasing contracture is considered to be a useful method for the patient since the level of surgical invasion is relatively low and restrictions in life caused by the treatment are small. However, the safety of the surgical procedure itself is not sufficiently ensured, and there is a room for improvement. The present invention contributes to enhancing the safety of percutaneous surgery for Dupuytren's contracture.

Hereinbelow, by referring to FIGS. 9 and 10, the operation for aponeurotic membrane incision for actual Dupuytren's contracture will be described. In percutaneous surgery for actual Dupuytren's contracture, the tip end portion 6 of the tissue perforation means 5 is inserted from a skin incision part 46, which has been incised in advance near the aponeurotic membrane 44 to be incised, in a minor-axis direction to a layer deeper than the aponeurotic membrane 44. In this situation, an ultrasonic diagnostic device is used. A probe 45 of the ultrasonic diagnostic device is placed on the palm to confirm the location of the nerve and blood vessel 35 and the tendon 33. By inserting the tissue perforation means 5 in a layer shallower than the aforementioned tissues under ultrasonic wave guidance, a safe subcutaneous path can be produced.

As in the case of Embodiment 1, the shape of the tissue perforation means 5 contributes to enabling one instrument to safely perform two types of operations: perforation and expansion. When perforating the aponeurotic membrane 44, the aponeurotic membrane 44 can be perforated with small resistance. A sufficient path can be produced so that the tip end portion 6, the expansion portion 7, and the parallel portion 8 of the tissue perforation means 5 can be inserted into a layer deeper than the aponeurotic membrane 44 and that the incised part reception means 2 can be inserted, below the skin 37, the aponeurotic membrane 44, and a tissue below the aponeurotic membrane. As in the case of Embodiment 1, the tissue perforation means 5 does not fall from the aponeurotic membrane 44 even when a relatively strong force is exerted for expansion during perforation.

As in the case of Embodiment 1, using the tissue perforation means 5, the surgeon can feel a resistance increase and decrease during expansion of the perforation portion in the middle of the procedure and can confirm each step of puncture and expansion of the aponeurotic membrane 44. After perforating the aponeurotic membrane 44, performing an operation using the bent provided at the tip end produces the advantage of allowing the tip end portion 6 to be inserted in parallel with the skin 37 and not damaging the nerve and blood vessel 35 or the tendon 33. The upper surface of the tip end portion 6 of the tissue perforation means 5 is a flat surface that preferably reflects an ultrasonic wave.

Figure 10:
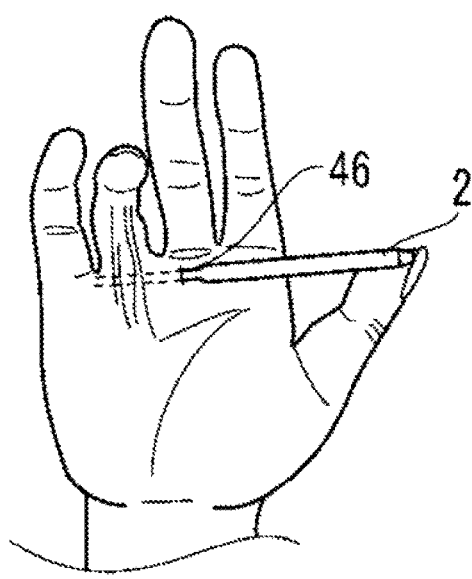
FIG. 10 is an illustrative disease state diagram illustrating a method of using the incised part reception means according to another embodiment of the surgical instrument for performing incision according to the present invention.
Figure 11:
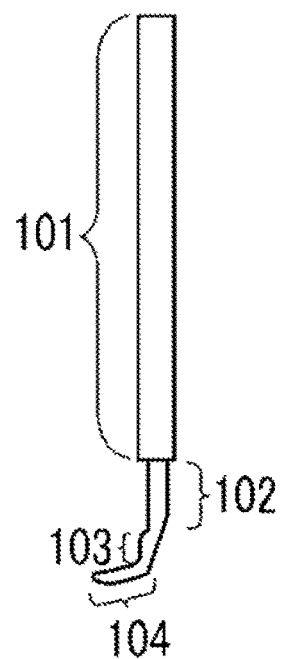
FIG. 11 is an explanatory diagram illustrating one embodiment of a conventional example.
Figure 12:
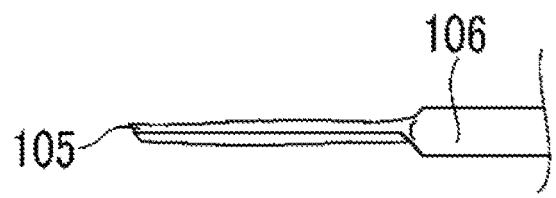
FIG. 12 is an explanatory diagram illustrating one embodiment of a conventional example.

After using the tissue perforation means 5 to form a path extending to an area deeper than the skin 37 and the aponeurotic membrane 44, as illustrated in FIGS. 9 and 10, the incised part reception means 2 is inserted in the minor axis direction from the same skin incision part 46 to a layer shallower than the tendon 33 and the nerve and blood vessel 35. In this series of procedures, combined use of an ultrasonic test device during the surgery is important for this surgery. Thereby, it is possible to confirm not only the incision range, but also the positional relationship between a tissue of the tendon 33, the nerve and blood vessel 35, and the like and the incised part reception means 2, and surgery can be safely performed.

The operation of the incised part reception means 2, the guide fixture means 3, and the Incision means hold means 4 is the same as that of Embodiment 1 and therefore is omitted here.

Hereinabove, embodiments of the surgical instrument for performing incision 1 according to the present invention have been described. However, this surgical instrument for performing incision 1 is not limited to the configurations illustrated in the aforementioned embodiments. It goes without saying that the surgical instrument for performing incision 1 can be appropriately modified within the scope of achieving an object of the present invention.

For example, the incised part reception means 2 and the tissue perforation means 5 are illustrated as separate members. However, these members may be integrated as one member that has the features of the two members.

As an example of the surgical instrument for performing incision 1 according to the present invention, an instrument including the tissue perforation means 5, the incised part reception means 2, the guide fixture means 3, the incision means hold means 4, and the incision means 28 has been described. However, the surgical instrument for performing incision 1 needs to include at least the incised part reception means 2, the guide fixture means 3, and the incision means 28. Regarding other elements, such as the tissue perforation means 5 and the incision means hold means 4, the members described in the aforementioned embodiments are preferable. However, generally used members are acceptable as well.

According to the present invention, there is provided a surgical instrument for performing incision that can be used for a similar target at any site in the body regardless of the aforementioned examples and whereby surgery can be readily performed in the same use method.

INDUSTRIAL APPLICABILITY

As described above, according to the present invention, a tendon sheath and aponeurotic membrane can be incised by puncturing only, instead of significantly incising skin or a subcutaneous tissue, and safe surgery with extremely small invasion is possible. Post-surgery damage, such as scarring of skin or a subcutaneous tissue, can thereby be reduced to a minimum. Stitching is not necessary, and restrictions due to suture wound management up to the time of stitch removal are decreased to contribute to enhancing the quality of life of the patient. The surgical instrument for performing incision can be widely used as surgery can be thereby readily performed by one surgeon and introduction into a small-sized hospital is possible.

REFERENCE SIGNS LIST 1 surgical instrument for performing incision
2 incised part reception means
3 guide fixture means
4 incision means hold means
5 tissue perforation means
6 tip end portion
7 expansion portion
8 parallel portion
9 handle portion
10 tip end portion.
11 incision table portion
11a guide groove
12 recessed portion
13 bent portion
14 handle portion
14a scale
15 base end portion
16 support column
17 arm portion
17a scale
18 slit
19 base portion
20 oblique hole portion
21 thinned portion
22 knurled knob
23 engagement portion
24 grip portion
24a groove
24b knurling
25 arm portion
26 axis portion
27 stripper bolt
28 incision means such as single-use injection needle (incision means)
29 needle base
30 needle tube
31 tip end
32 bone
33 finger flexor tendon (tendon)
34 synovial tendon sheath
35 nerve and blood vessel
36 subcutaneous tissue
37 skin
38 ligament tendon sheath, (tendon sheath)
38a A1 pulley
39 metacarpal bone
40 coxal bone
41 MP joint
42 skin puncture part
43 skin incision part
44 palm aponeurotic membrane (aponeurotic membrane)
44a pathogenic aponeurotic membrane
45 probe
46 skin incision part
101 grip
102 shaft
103 blade portion
104 guide portion
105 blade portion
106 handle portion

The invention claimed is:
1. A surgical instrument for performing incision, comprising:
an incised part reception means including a handle portion at one end and an incision table portion with a guide groove running in a longitudinal direction at the other end, the incision table portion being configured to be inserted into a body from a skin surface area near an area subjected to treatment and is configured to receive an incised part of a tendon sheath and an aponeurotic membrane;
a guide fixture means including a base portion at one end, a downwardly protruding support column portion at the other end, and an arm portion bridging between the base portion and the downwardly protruding support column portion to form an escape space below the arm portion between the base portion and the downwardly protruding support column portion so that the arm portion is configured to cover the area subjected to treatment,
wherein the arm portion includes a slit that is configured to face the area subjected to treatment and extends along the guide groove of the incised part reception means,
wherein the base portion and the downwardly protruding support column portion are configured to fix the arm portion outside the body; and an incision means having a needle as a cutter that is configured to pass through the slit of the arm portion and the escape space and to be pressed onto the incision table portion of the incised part reception means substantially perpendicular to the incision table portion of the incised part reception means and to be movable to incise the tendon sheath and the aponeurotic membrane, wherein the needle of the incision means is configured to run along the guide groove and the slit.

2. The surgical instrument for performing incision according to claim 1, further comprising;

a tissue perforation means that is configured to be inserted into the body from the skin surface area near the area subjected to treatment that has been incised in advance to form an insertion path to an area near a site to be treated, wherein the incised part reception means is configured to be inserted into the insertion path formed by the tissue perforation means.

3. The surgical instrument for performing incision according to claim 1, further comprising an incision means hold means that holds the needle of the incision means.

4. The surgical instrument for performing incision according to claim 3, wherein the incision means hold means includes:
an axis portion including an engagement portion on which the needle of the incision means is mounted to hold the same;
a main body portion that fixes or swingably supports the axis portion; and
a fasten means that loosely fastens the axis portion to the main body portion.

5. The surgical instrument for performing incision according to claim 1, wherein:

the incised part reception means includes a bent portion between the handle portion and the incision table portion.

6. The surgical instrument for performing incision according to claim 5, wherein the incised part reception means further includes a recessed portion at a tip end of the guide groove of the incision table portion.

7. The surgical instrument for performing incision according to claim 5, wherein the base portion of the guide fixture means is configured to hold and fix the handle portion of the incised part reception means.

8. The surgical instrument for performing incision according to claim 5, further comprising:

a scale that is provided on the handle portion of the incised part reception means, and another scale that is provided on the arm portion of the guide fixture means so that both the scales are synchronized with each other to identify a location of the incision table portion of the incised part reception means fixed to the guide fixture means.

9. The surgical instrument for performing incision according to claim 5, wherein:

the tissue perforation means includes
a handle portion at one end, and
an insertion portion at the other end;
the insertion portion has a sharp tip end portion and an expansion portion whose width is greater than that of the tip end portion; and
the insertion portion bends smoothly toward the handle portion so as to have a bent portion similarly to the bent portion of the incised part reception means, and a bottom surface portion of the insertion portion is in a circular arc shape.

* * * * *